United States Patent [19]

Hoffman et al.

[11] Patent Number: 5,415,903
[45] Date of Patent: May 16, 1995

[54] SELF-ADHESIVE LAMINATE FOR TOE AND FINGERNAILS

[75] Inventors: Hans-Rainer Hoffman; Reinhard von Kleinsorgen, both of Neuwied; Guenter Simon, Hillesheim; Dorothea Steinborn, Neuwied, all of Germany

[73] Assignee: LTS Lohmann Therapie-Systeme GmbH & Co. KG, Neuwied, Germany

[21] Appl. No.: 192,802

[22] Filed: Feb. 7, 1994

Related U.S. Application Data

[63] Continuation of Ser. No. 825,105, Jan. 24, 1992, abandoned.

[30] Foreign Application Priority Data

Jul. 30, 1990 [DE] Germany ............... 40 24 125.4
Dec. 12, 1991 [DE] Germany ............... 41 40 888.8

[51] Int. Cl.$^6$ ............................................. A01N 1/00
[52] U.S. Cl. .................................. 428/15; 428/16; 428/195; 428/914; 156/245; 156/246; 156/289; 132/73
[58] Field of Search ............ 428/15, 16, 195, 913, 428/914; 132/73, 885; 156/245, 246, 289

[56] References Cited

U.S. PATENT DOCUMENTS

| | | | |
|---|---|---|---|
| 2,288,386 | 6/1942 | Belden | 132/3.317 |
| 2,746,460 | 5/1956 | Jellinek | 133/73 |
| 2,764,166 | 9/1956 | Bogoslowsky | 132/73 |
| 2,864,384 | 12/1958 | Walter | 133/73 |
| 2,979,061 | 4/1961 | Greenman | 133/73 |
| 4,682,612 | 7/1987 | Giuliano | 132/73 |
| 4,824,702 | 4/1989 | Straub | 428/15 |
| 4,876,121 | 10/1989 | Cohen | 428/15 |
| 4,903,840 | 2/1990 | So | 206/581 |
| 4,947,876 | 8/1990 | Larsen | 133/73 |
| 5,044,384 | 9/1991 | Hokama et al. | 132/200 |
| 5,225,185 | 7/1993 | Castrogiovanni | 424/61 |

FOREIGN PATENT DOCUMENTS

| | | | |
|---|---|---|---|
| 2362818 | 6/1974 | Germany | A45D 31/00 |
| 3337458 | 4/1985 | Germany | A45D 31/00 |
| 340592 | 8/1959 | Switzerland | A45D 31/00 |

*Primary Examiner*—Patrick J. Ryan
*Assistant Examiner*—William A. Krynski
*Attorney, Agent, or Firm*—Jacobson, Price, Holman & Stern

[57] ABSTRACT

The invention relates to a self-adhesive laminate, shapeable to toe and fingernails, containing a) a film-forming polymer layer containing at least one plasticizer, b) a pressure-sensitive adhesive layer located thereon, and c) a carrier film which covers the pressure-sensitive adhesive layer and can be removed again, wherein the film-forming layer a) is also covered on the other side, at least over the entire surface, with d) a protective layer, which is likewise removable and is resistant to the other constituents of the laminate and the materials used in the preparation of the laminate.

The invention also relates to a process for the preparation of such a laminate and to its use for application to toenails or fingernails as synthetic nails.

44 Claims, 1 Drawing Sheet

SELF-ADHESIVE LAMINATE FOR TOE AND FINGERNAILS

This application is a continuation of application Ser. No. 07/825,105, filed Jan. 24, 1992, now abandoned.

RELATED APPLICATION

This application is a continuation-in-part of international application No. PCT/EP/91/01402, filed Jul. 26, 1991.

The invention relates to a self-adhesive laminate, shapeable to toe and fingernails, consisting of
a) a film-forming polymer layer containing at least one plasticizer,
b) a pressure-sensitive adhesive layer located thereon,
c) a carrier film or supporting foil which covers the pressure-sensitive adhesive layer and can be removed again, and
d) a protective layer d) located on the other side of the polymer layer a),
a process for its preparation and its use for application to toe and fingernails as artificial nails.

It is known to treat nails using solvent-containing polymer varnishes to achieve a cosmetic effect (nail varnish). It is also known to add to such a varnish a substance having an antimycotic action or an active substance which cares for the nails.

It is also generally known how much effort it takes to apply such a nail varnish with the desired appearance (time, drying of the varnish, practice, external appearance).

Many consumers find the organic solvent content in known nail varnishes to be a nuisance. In particular, however, in view of the high worldwide consumption, it constitutes an appreciable environmental pollution, which for reasons of environmental protection should be avoided or at least reduced. On these grounds alone, the use of a decorative film for application to nails, in conjunction with the characteristics demanded by the consumer, such as gloss effect, color effect, stability, wearability and naturalness, as a replacement for the solvent-containing varnish should be recognized as a sensible alternative.

The use of artificial nails, as always bonded to the nail, is known.

It is also known from DE-OS 23 62 818 to stick an adhesive film, for example one made of polyvinyl chloride (PVC) or a material having similar properties, to the nails. However, a system of this type has not found acceptance on the market because the polymer material mentioned in this publication does not meet consumer expectations with respect to gloss, hardness, flexibility and stability on the nail. The high tear strength of the PVC film or similar polymer films, such as polyethylene, polypropylene or polyester, makes it more difficult to shape the film to the nail by means of simple filing and involves the risk of injury to the nail bed.

The shapeability to the nail and also the stability with regard to the means of application are directly related to the brittleness of the laminate and it had to be realized that the ideal characteristics of a nail varnish laminate (laminate in particular based on nitrocellulose—commercial nail varnish) raise stability problems such that the laminate becomes brittle on storage (dries out) and can no longer be applied.

The object of the present invention was, therefore, to develop a self-adhesive laminate which is comparable with the commercially available solvent-based nail varnishes, has the corresponding characteristics desired by the consumer, such as gloss, hardness, flexibility, stability on the nail and without the sensation of a foreign body, which is shapeable on the nail and which, together with the abovementioned characteristics, has an adequate stability towards drying out and the excessive brittleness caused as a result.

It proved difficult to achieve this object, in particular the combination of adequate stability coupled, at the same time, with adequate surface hardness and flexibility, since these characteristics are mutually opposing. If a stable laminate is achieved, this does not have adequate surface hardness because of the large amount of plasticizer added. If the surface hardness is adequate, the laminate, on the other hand, so rapidly becomes brittle on storage that application is no longer possible because of the brittleness of the laminate.

Surprisingly, it has been found that the combination of these characteristics which are important for use is achieved if a solvent-containing varnish, preferably a varnish based on nitrocellulose and/or acrylates, is first applied to a cover film, the varnish is then dried, with recovery of at least the bulk of the solvent, and this combination is laminated on the varnish side with an adhesive film and a protective layer. The term "acrylates" should also be understood to include alkyl-substituted compounds, such as methacrylates.

The subject of the invention is, thus, a self-adhesive laminate, shapeable to toe and fingernails, containing
a) a film-forming polymer layer containing at least one plasticizer,
b) a pressure-sensitive adhesive layer located thereon, and
c) a carrier film or supporting foil which covers the pressure-sensitive adhesive layer, can be removed again and is preferably silicone-treated,
wherein the film-forming polymer layer a) is also covered on the other side, at least over the entire surface, with
d) a protective layer, which is likewise removable and is resistant to the other constituents of the laminate and the materials used in the preparation of the laminate.

The laminate according to the invention can thus be used for fingernails or toenails, or both, as desired.

Figure 1:
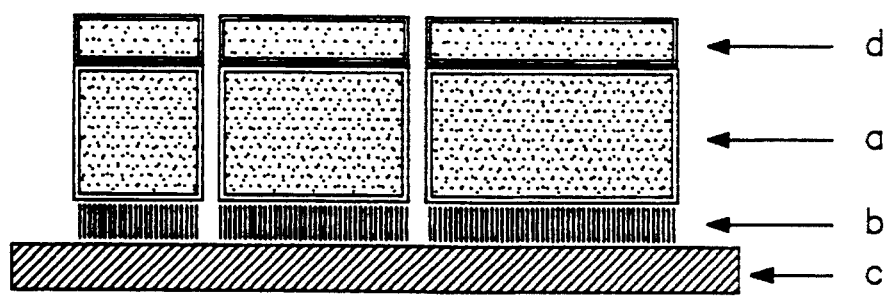
FIG. 1 shows a cross-section of a card containing three regions, as described in Example 1.

The coating of the varnish (that is to say the polymer layer) onto the protective layer, to be removed before application, on the one hand enables structuring of the surface of the polymer layer and on the other hand it ensures the stability and suitability for use of the laminate up to the time of application. The surface structuring of the polymer layer corresponds to a negative mold.

The size of the protective layer d) corresponds at least to the size of the laminate and is preferably larger. The protective layer can consist of a film, preferably a plastic film, or a paper or of a textile sheet-like structure. Advantageously, it consists of a transparent material in order to prevent mistakes in respect of the color on application. It can have a single layer or multi-layer structure, it being possible for the layers to be of different composition. For example, it can thus consist of a paper sheet coated with one of the abovementioned plastics.

Suitable plastic films are, for example, films made of polyesters, such as polyethylene terephthalate, polybutylene terephthalate or polyethylene sebacate, or made of polyethylene, polypropylene or polyamides, such as polyhexamethylene adipate, polycaprolactam or poly(ω-undecanoic acid amide). Because of their surface characteristics, these plastics are, of course, not yet removable again. In order to impart this characteristic, a surface treatment with suitable substances, such as a silicone treatment or, which is a particularly preferred embodiment within the framework of the present invention, a treatment with salts of long-chain fatty acids having, for example, 12 to 22 carbon atoms, which acids are saturated or can contain up to three olefinic bonds, and at least divalent metals, especially transition heavy metal salts of this type, and amongst these in particular the chromium salts, is advantageous.

The textile sheet-like structure can be a nonwoven or woven fabric, which appropriately has been provided with an adhesive finish.

The protective layer d) is preferably provided with a non-stick finish on the side coated with the polymer layer a), that is to say the adhesion between the protective layer and the laminate is lower than the adhesion between adhesive layer and carrier film. Advantageously, the carrier film is provided with a pull-off aid, for example by providing semicircular cutouts therein. Handling is facilitated as a result.

The adhesive layer b) of the laminate can consist of a known adhesive composition and can likewise be single layer or multi-layer. The weight per unit area of the adhesive layer is in general in the range from 20 to 100 g/m$^2$, preferably 25 to 75 g/m$^2$.

The polymer layer of the laminate, which can be single layer or also multi-layer, generally has a layer thickness of 25 to 200, preferably 60 to 150 μm, it being possible for the individual layers to have a different composition in the case of a multi-layer structure.

The plasticizer content in the polymer layer (the adhesive layer can also contain the same or a different plasticizer) is generally 1 to 30, preferably 15 to 25 and in particular 17 to 22% by weight, based on the polymers.

The plasticizers preferably used are those which have only extremely small migration, such as conventional citric acid esters or dioctyl adipate. Camphor can optionally be used as an additional plasticizer, but this is not preferred. In this case, the preferred amount of plasticizer is 5 to 12.5, in particular 7 to 10% by weight. Since the polymer layer a) is often produced from conventional nail varnishes, it frequently also contains yet further plasticizing compounds, such as phthalates, for example dibutyl phthalate.

The polymer layer advantageously consists, at least in part, of nitrocellulose on its own or acrylates on their own or mixtures of these two components which are known per se for nail varnishes. The acrylates used are in particular polymers of acrylic acid esters or methacrylate acid esters, in particular of alcohols having 1 to 4, preferably 1 to 2 C atoms, and/or dimethylaminoethyl methacrylate. The polymer layer usually also contains at least one colorant customary in the cosmetics industry, that is to say dyes and/or pigments; however, this is not necessary. The self-adhesive laminates according to the invention can, specifically, also be transparent, if this is desired.

Additives, such as odor-active components (fragrance) and/or active compounds, preferably substances having an antimycotic action, such as clotrimazole, miconazole, ketoconazole, econazole, naftifine, ciclopirox olamaine, fenticlor, sulbentine, tolnaftate and haloprogin can also be added to the polymer layer a) and/or the adhesive layer b). In cases of this type, the adhesive layer advantageously consists of several layers.

According to the invention, compounds of the formula

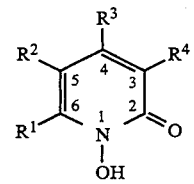

as are described in EP 226 984 (=U.S. Pat. No. 4,957,730) as constituents in nail varnishes for the purpose of treatment of onychomnicoses, can also be used as active substances. According to the said patent specification, these nail varnishes are applied in liquid form. In the compounds mentioned, $R^1$ denotes a hydrocarbon group which contains 6 to 9 carbon atoms but is free from olefinic and acetylenic bonds; one of the groups $R^2$ and $R^4$ denotes hydrogen and the other denotes hydrogen, methyl or ethyl, and $R^3$ is alkyl having up to 2 C atoms; these active compounds can be present in the free form or in the form of a salt. $R^1$ can be, for example, a cyclohexyl or octyl group, for example of the formula $CH_2-CH(CH_3)-CH_2-C(CH_3)_3$. Compared with the varnishes as claimed in EP 226 954, the incorporation of the said compounds in the laminates according to the invention has the advantages that the bioavailability of the active compound from the laminate in the particular degree desired is ensured by the standardized layer thickness and that the period of action can be arbitrarily adjusted by means of the thickness of the laminate. As it was possible to confirm by in vitro experiments, the adhesive layer of the laminate according to the invention is permeable for the said active compounds, that is to say constitutes no barrier to said compounds if said active compounds are present in the polymer layer. On the contrary, the action of the active compounds on the nail can be further accelerated if the active compound is also incorporated in the adhesive layer.

The adhesive layer can also contain a substance which promotes the penetration of the active compound into the nail. The addition of penetration accelerators or enhancers to an active compound/adhesive formulation is known from the field of transdermal therapeutic systems. Substances which promote the transport of an active compound into the skin or through the skin are, for example, dimethyl sulfoxide (DMSO) and dimethylformamide (DMF) as well as a large number of different emulsifiers, fatty acids and their esters.

The invention also relates to a process for the preparation of the self-adhesive laminates, wherein a varnish, which contains at least one plasticizer, at least one film-forming polymer, dissolved or dispersed in an organic solvent, and advantageously also a colorant, that is to say dyes and/or pigments, is applied to a protective layer d), which can be pulled off and which is of at least the same size as the laminate, the varnish is dried, with recovery of the solvent, and the protective layer d) coated with the varnish is laminated on the varnish side with an adhesive film b) and a carrier film c).

The invention has the following advantages: no organic solvent is released into the environment. The laminates according to the invention, which are suitable as artificial toenails or fingernails, meet all of the requirements specified for them on the part of the consumer, in respect of gloss, hardness, flexibility and stability. Their characteristics are such that injury to the nail bed during application and use is prevented. Moreover, as a result of the use of a suitable structured cover layer, the polymer layer can also be structured for decorative purposes. Finally, the invention also relates to the use of the laminates according to the invention as artificial toenails or fingernails.

Figure 2:
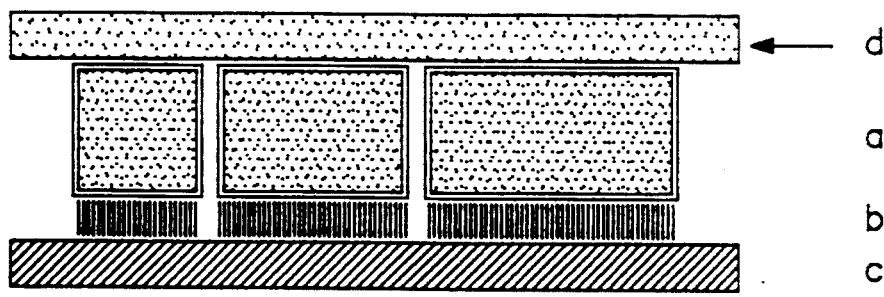
FIG. 2 shows a laminate in cross-section, where the protective layer d) overlappingly covers several regions.
Figure 3:
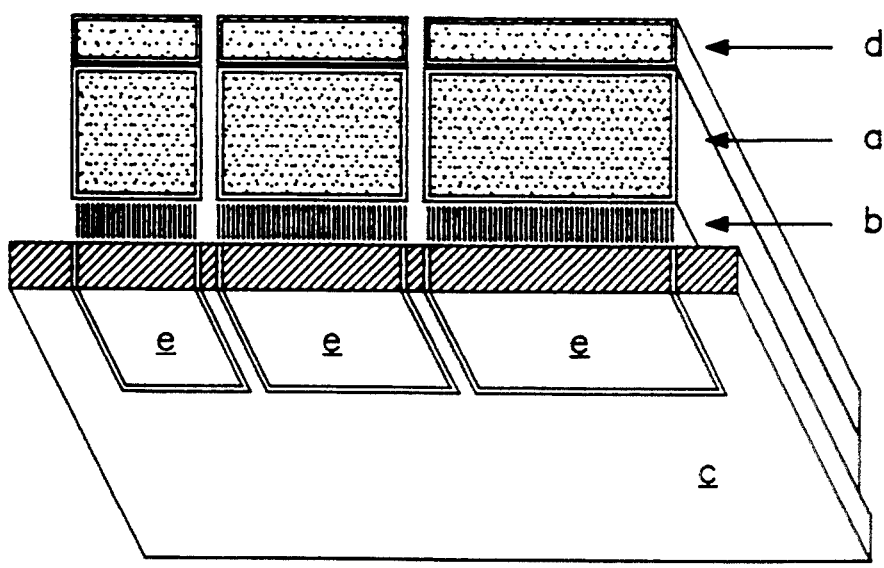
FIG. 3 shows the plan view of one region, the carrier film c) having the pull-off aid e).

The invention is illustrated in a non-limiting manner with reference to FIGS. 1 to 3 and by the following examples:

As described in Example 1, a polymer layer a) (pigmented nail varnish, layer thickness, for example, 200 μm) is arranged on a protective layer d) (polyester film 100 μm thick which has a partially structured surface and is to be removed before application) and an adhesive layer b) (based on polyisobutylene, layer thickness, for example, 80 μm) is arranged on the polymer layer a). The laminate is provided with a carrier film c).

EXAMPLE 1 a) Polymer layer—a commercially available nail varnish composition consisting of

| | |
|---|---|
| 136.5 g | of nitrocellulose (as rigid polymer) |
| 50.0 g | of polyacrylate (®Acronal 2F from BASF AG, Ludwigshafen, as flexible polymer) |
| 50.0 g | of toluenesulfonamide resin (®Santolite MHP from Monsanto, USA) |
| 23.0 g | of plasticizer (citric acid ester, ®Citroflex A from Pfizer, USA) |
| 60.0 g | of dibutyl phthalate |
| 210 g | of ethyl acetate |
| 200 g | toluene |
| 100 g | of butyl acetate |
| 77 g | of ethanol |
| 73.5 g | of n-butanol, and |
| 20 g | of commercially available color pigment used in the cosmetics industry |
| 1000 g | | is applied to a silicone-treated protective layer d) (50 μm polyethylene terephthalate film) and dried (thickness of the polymer layer 200 μm).

b) Pressure-sensitive adhesive layer—an adhesive composition is prepared from the following constituents:

0.153 kg of polyisobutylene (average molecular weight of 900,000 to 1,400,000—ᴿOppanol B 100 from BASF AG, Ludwigshafen)

0.137 kg of solid aliphatic hydrocarbon resin (melting point 100° C.—ᴿHercures C from Hercules, Wilmington, Del., USA)

0.137 kg of liquid hydrogenated rosin (ᴿAbitol from Hercules, Wilmington, Del., USA)

0.005 kg of stabilizer (antioxidant)

1.148 kg of special benzine (boiling point 80°–110° C.) as solvent.

This composition is applied to a carrier film (polyester film), provided with an adhesive finish on one side, and dried (adhesive layer thickness 80 μm).

Regions are punched through the protective layer d), the polymer a) and the pressure-sensitive adhesive layer b) in the laminate obtained in this way, without punching through the carrier film c). The dimensions of the regions approximately correspond to those of different fingernails. The intermediate links between the regions are removed. The laminate obtained in this way can be divided by cutting in such a way that laminate cards, designated cards below, are obtained which have at least 10 regions and specifically one region for each fingernail of both hands.

The laminate prepared in this way proved stable on storage for 6 months at 50° C. and met the requirements in respect of application and wear characteristics. Products without protective layer d) became brittle after storing for only 2 days at 50° C. and could no longer be applied.

The laminates prepared in this way are applied to the nails as follows:

In order to treat a nail, one region is removed from the carrier film c) by means of the pull-off aid and stuck on the nail. The protective layer d) is removed subsequently or simultaneously with sticking on, and the self-adhesive polymer layer a) is then shaped on the nail.

If the protective layer d) forms a coherent covering over several regions, it can be removed from the carrier film c) for the removal of a region of the self-adhesive polymer layer.

After application, the polymer layer provided with the pressure-sensitive adhesive has the same characteristics as a layer of varnish which has been applied by means of a solvent-containing nail varnish composition, but, in contrast to sticking on so-called artificial fingernails, there is no sensation of a foreign body in the case of the product according to the invention.

The polymer layer provided with the pressure-sensitive adhesive can be pulled off a nail again, by, for example, sticking a self-adhesive film on top of the polymer layer and, after pressing the film to the edges of the polymer layer, pulling this off the nail in its entirety, that is to say in a manner similar to the way in which price labels on packaging can be removed by means of a self-adhesive tape. No residue remains on the nail, so that it is unnecessary to clean the nail with an organic solvent. This is a significant advantage in the case of the use of the laminates according to the invention. As a result of this new application system, the so-called "staining" phenomenon, that is to say the penetration of colorant into the nail, which frequently arises in the case of nail varnishes, is also prevented, which constitutes a further significant advantage.

EXAMPLE 2

Example 1 is modified to the extent that a pressure-sensitive adhesive composition b) is used which consists of 2.08 kg of a 40% strength solution of a self-crosslinking acrylate copolymer of 2-ethylhexyl acrylate, vinyl acetate, acrylic acid and titanium chelate ester in a mixture in ethyl acetate, ethanol, hexane and methanol, 147 g of an acrylic resin obtained from dimethylaminoethyl methacrylate and neutral methacrylic ester and 20 g of a mixed acid triglyceride of fractionated $C_8$–$C_{10}$ coconut fatty acids.

EXAMPLE 3

Example 1 is modified to the extent that the polymer layer specified in that example is applied to a 50 μm thick protective layer d), composed of polyethylene terephthalate film treated with 1 to 2 g/m² of a chromium stearate complex (RQuilon C from du Pont, Wilmington, Del., USA), and dried (thickness of the polymer layer likewise 200 μm). Compared with laminates which have been prepared using a silicone-treated film, the laminate prepared using this product has the additional advantage that the protective layer can be removed even more easily, subsequently or at the same time as the laminate is stuck onto the nail.

We claim:

1. A self-adhesive laminate which is adjustable in form to that of toe nails or finger nails and which comprises:
   (a) a film-forming polymer layer comprising nitrocellulose and containing a plasticiser,
   (b) an adhesive layer covering one side of said polymer layer and being present in an amount of from 20 to 100 g/m²,
   (c) a supporting foil covering the adhesive layer (b) and being completely detachable therefrom, the film-forming polymer layer (a) being additionally completely covered, on its reverse side, with
   (d) a protective layer which is adhered to but completely detachable from the film-forming polymer layer and is chemically resistant towards the other components of the laminate and the compounds used in the manufacture thereof, the adhesion of the protective layer (d) to the polymer layer (a) being less than the adhesion between the adhesive layer (b) and supporting foil (c).

2. A self-adhesive laminate of claim 1 in the form and shape of a toenail or fingernail.

3. A laminate as claimed in claim 1, wherein the protective layer is furnished with a pattern.

4. A laminate as claimed in claim 1, wherein the protective layer consists of a foil comprising a synthetic resin, of paper or of textile material.

5. A laminate as claimed in claim 1, wherein the protective layer (d) is a transparent one.

6. A laminate as claimed in claim 1, wherein the polymer layer (a) or the protective layer (d) or both comprise a plurality of layers.

7. A laminate as claimed in claim 6, wherein the plurality of layers of at least one of layer (a) and layer (d) differ in composition.

8. A laminate as claimed in claim 1, wherein the supporting foil (c) is furnished with a pull-off aid means enabling its detaching.

9. A laminate as claimed in claim 1, wherein the adhesive layer (b) is present in an amount of 25 to 75 g/m².

10. A laminate as claimed in claim 1, wherein the polymer layer (a) has a thickness of in the range from 25 to 200 μm.

11. A laminate as claimed in claim 10, wherein the thickness is in the range from 60 to 150 μm.

12. A laminate as claimed in claim 1, wherein the plasticiser is present in the polymer layer (a) in an amount of from 1 to 30%, calculated on the weight of the polymer.

13. A laminate as claimed in claim 12, wherein the amount is in the range of from 15 to 25% by weight.

14. A laminate as claimed in claim 13, wherein the amount is in the range of from 17 to 22% by weight.

15. A laminate as claimed in claim 1, wherein layer (a) further comprises, as colorant, a dyestuff or a pigment or a combination of both.

16. An artificial nail for a toe or finger comprising a self-adhering laminate which is a laminate of claim 1.

17. A self-adhesive laminate of claim 1 wherein the plasticizer is one for which the migration is of the same order of magnitude, in context, as that of conventional citric acid esters or dioctyl adipate.

18. A self-adhesive laminate which is adjustable in form to that of toe nails or finger nails and which comprises:
   (a) a film-forming polymer layer containing a plasticiser,
   (b) an adhesive layer covering one side of said polymer layer,
   (c) a supporting foil covering the adhesive layer (b) and being adhered to but completely detachable therefrom,
the film-forming polymer layer (a) being additionally completely covered, on its reverse side, with
   (d) a protective layer consisting of a synthetic resin, which layer is adhered to but completely detachable from the film-forming layer and is chemically resistant towards the other components of the laminate and the compounds used in the manufacture thereof,
the polymer layer (a), the protective layer (d) or both being composed of a plurality of layers of different composition, the content of the plasticiser in the polymer layer (a) being in the range of from 1 to 30%, calculated on the weight of the polymer, and the layer (d) being additionally coated with a layer comprising, as an essential ingredient, a complex salt of a fatty acid of from 12 to 22 carbon atoms which is saturated or contains up to three olefinic bonds, and an at least bivalent heavy transition metal.

19. A laminate as claimed in claim 18, wherein the heavy transition metal is chromium.

20. A process for the manufacture of a self-adhering laminate being adjustable to the form of the nails of the toes and fingers which comprises applying a nail varnish which contains at least one plasticiser and at least one film-forming polymer dissolved or dispersed in an organic solvent onto a part or the whole surface of a detachable protective layer (d), drying the varnish while recovering the solvent, and laminating the dried varnish with an adhesive layer (b) and subsequently with a supporting foil (c).

21. A process as claimed in claim 20, wherein the nail varnish contains a dyestuff or a pigment or a combination thereof.

22. A process of claim 20 which further comprises shaping the resulting laminate in the form of a toenail or of a fingernail.

23. An artificial nail for a toe or finger comprising a self-adhering laminate which is adjustable in form to that of a toe or finger nail and containing as essential components
   (a) a film-forming polymer layer containing a plasticizer and
   (b) an adhesive layer completely joined with said polymer layer,
said laminate being provided with
   (c) a supporting foil covering the adhesive layer (b) and being adhered to but completely detachable therefrom, and the side of the film-forming polymer layer which is not in contact with the adhesive layer, being completely covered by
 (d) a protective layer which is completely detachable form the film-forming polymer layer.

24. A self adhesive laminate which is adjustable in form to that of toenails or fingernails and which comprises:
 a) a film-forming polymer layer containing an ester of citric acid as a plasticizer,
 b) an adhesive layer covering one side of said polymer layer,
 c) a supporting foil covering the adhesive layer (b) and being completely detachable therefrom,
the film-forming layer (a) being additionally covered, on its reverse side, with
 d) a protective layer which is adhered to but completely detachable from the film-forming polymer layer and is chemically resistant towards the other components of the laminate and the compounds used in the manufacture thereof.

25. A laminate as claimed in claim 24, wherein the plasticiser is present in the polymer layer (a) in an amount of from 1 to 25 percent, calculated on the polymer in layer (a).

26. A laminate as claimed in claim 25, wherein the film-forming polymer contains camphor as an additional plasticiser.

27. A laminate as claimed in claim 26, wherein the plasticiser is present in the polymer layer (a) in an amount of from 5 to 12.5 percent by weight.

28. A laminate as claimed in claim 26, wherein the polymer layer (a) comprises nitro-cellulose.

29. A self-adhesive laminate which is adjustable in form to that of toe nails or finger nails and which comprises
 (a) a film-forming polymer layer containing a plasticiser and being derived from a nail varnish free from camphor,
 (b) an adhesive layer covering one side of said polymer layer,
 (c) a supporting foil covering the adhesive layer (b) and being completely detachable therefrom,
the film-forming polymer layer (a) being additionally completely covered, on its reverse side, with
 (d) a protective layer which is adhered to but completely detachable from the film-forming polymer layer and is chemically resistant towards the other components of the laminate and the compounds used in the manufacture thereof.

30. A self-adhesive laminate which is adjustable in form to that of toe nails or finger nails and which comprises:
 (a) a film-forming polymer layer containing a plasticiser,
 (b) an adhesive layer covering one side of said polymer layer,
 (c) a supporting foil covering the adhesive layer (b) and being completely detachable therefrom,
the film-forming polymer layer (a) being additionally completely covered, on its reverse side, with
 (d) a protective layer which is adhered to but completely detachable from the film-forming polymer layer and is chemically resistant towards the other components of the laminate and the compounds used in the manufacture thereof, the polymer layer (a) or the adhesive layer (b) or both containing a fragrant or a pharmaceutically active compound or both.

31. A laminate as claimed in claim 30, wherein the polymer layer (a) comprises nitro-cellulose, an acrylate polymer or a methacrylate polymer.

32. A laminate as claimed in claim 31, wherein the acrylate polymer and the methacrylate polymer contain an alcohol component having from 1 to 4 carbon atoms each or wherein the methacrylate polymer is a polymer of dimethylaminoethylmethacrylate.

33. A laminate as claimed in claim 32, wherein the alcohol component contains from 1 to 2 carbon atoms.

34. A laminate as claimed in claim 30, wherein the pharmaceutically active compound is an antimycotic compound.

35. A laminate as claimed in claim 34, a) wherein the antimycotic compound is clotrimazol, miconazol, ketoconazol, econazol, naftidin, fenticlor, sulbentin, tolnaftat, haloprogin or a combination thereof, or b) wherein the anti-mycotic compound is a 1-hydroxy-2-pyridone according to the formula

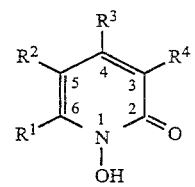

in which $R^1$ is a hydrocarbon group which contains from 6 to 9 carbon atoms, but said hydrocarbon group being free from olefinic and acetylenic bonds, one of the groups $R^2$ and $R^4$ is hydrogen and the other is hydrogen, methyl or ethyl and $R^3$ is alkyl having up to two carbon atoms, said antimycotic ingredient being present in free form or in the form of a salt, and in an amount effective against nail mycoses.

36. A laminate as claimed in claim 30, wherein the adhesive layer (b) contains a penetration enhancing component for the pharmaceutically active compound.

37. A laminate as claimed in claim 36, wherein the said penetration enhancing component is dimethylsulfoxide or dimethylformamide.

38. An artificial nail for a toe or finger comprising a self-adhering laminate which is a laminate of claim 30.

39. A self-adhesive laminate which is adjustable in form to that of toe nails or finger nails and which comprises:
 (a) a film-forming polymer layer containing a plasticiser,
 (b) an adhesive layer covering one side of said polymer layer,
 (c) a supporting foil covering the adhesive layer (b) and being completely detachable therefrom,
the film-forming polymer layer (a) being additionally completely covered, on its reverse side, with
 (d) a protective layer which is adhered to but completely detachable from the film-forming polymer layer, is chemically resistant towards the other components of the laminate and the compounds used in the manufacture thereof, and has been finished on the side adjacent to the polymer layer (a) with an agent for reducing adhesivity, the adhesion of the protective layer (d) to the polymer layer (a) being less than the adhesion between the adhesive layer (b) and supporting foil (c).

40. A laminate as claimed in claim 30, wherein the agent providing reduced adhesivity comprises, as an essential ingredient, a complex salt of a fatty acid of 12 to 22 carbon atoms which is saturated or contains up to three olefinic bonds, and an at least bivalent metal.

41. A laminate as claimed in claim 40, wherein the at least bivalent metal is a heavy transition metal.

42. A laminate as claimed in claim 41, wherein the heavy transition metal is chromium.

43. A laminate as claimed in claim 30, wherein the layer (d) is coated with a silicone.

44. A self-adhesive laminate which is adjustable in form to that of toe nails or finger nails and which comprises
    (a) a film-forming polymer layer containing a plasticizer, the migration of which, in context, is substantially the same as that of conventional citric acid esters or dioctyl adipate,
    (b) an adhesive layer covering one side of said polymer layer,
    (c) a supporting foil covering the adhesive layer (b) and being completely detachable therefrom,
the film-forming layer (a) being additionally covered, on its reverse side, with
    (d) a protective layer which is adhered to but completely detachable from the film-forming polymer layer and is chemically resistant towards the other components of the laminate and the compounds used in the manufacture thereof.

* * * * *